| United States Patent [19] | [11] Patent Number: 4,565,864 |
| Wade | [45] Date of Patent: Jan. 21, 1986 |

[54] SUBSTITUTED IMIDAZO[1,2-C]PYRIMIDINES

[75] Inventor: James J. Wade, Oakdale, Minn.

[73] Assignee: Riker Laboratories, Inc., St. Paul, Minn.

[21] Appl. No.: 682,663

[22] Filed: Dec. 17, 1984

Related U.S. Application Data

[62] Division of Ser. No. 500,410, Jun. 2, 1983, Pat. No. 4,503,050.

[51] Int. Cl.$^4$ .................. C07D 417/04; C07D 403/04
[52] U.S. Cl. ..................................... 544/58.2; 544/60; 544/122; 544/295; 544/317; 544/326
[58] Field of Search ................ 544/58.2, 60, 122, 295, 544/317, 326

[56] References Cited

PUBLICATIONS

Sazonov et al., Chemical Abstracts, vol. 68 (1968) 114,541m.
Nishigaki et al., Chemical Abstracts, vol. 73 (1970) 66530m.
Nantka–Namirski et al., Chemical Abstracts, vol. 74 (1971) 31766m.
Nishigaki et al., Chemical Abstracts, vol. 74 (1971) 111,997c.
Rasmussen et al., Chemical Abstracts, vol. 90 (1979) 86292q.
Fletcher, Chemical Abstracts, vol. 94 (1981) 123,120n.

*Primary Examiner*—Richard L. Raymond
*Attorney, Agent, or Firm*—Donald M. Sell; James A. Smith; Robert W. Sprague

[57] ABSTRACT

Imidazo[1,2,-c]pyrimidines which are bronchodilators. Pharmacological methods of using these compounds, pharmaceutical compositions containing these compounds, and synthetic intermediates for preparing these compounds are also described.

2 Claims, No Drawings

SUBSTITUTED IMIDAZO[1,2-C]PYRIMIDINES

This is a division of application Ser. No. 500,410 filed June 2, 1983, now U.S. Pat. No. 4,503,050.

TECHNICAL FIELD

The present invention relates to imidazo [1,2-c]-pyrimidines. Pharmocological methods of using these compounds as bronchodilators, pharmaceutical compositions comprising these compounds and synthetic intermediates in the preparation of these compounds are also included within the scope of the invention.

BACKGROUND OF THE INVENTION

Certain imidazo [1,2-c]pyrimidines are known to the art.

Noell et al., *J. Heterocyclic Chem.*, 1, 34 (1964), prepared 2,7-dichloro-5-methylthioimidazo-[1,2-c]pyrimidine, 2,5,7-trichloroimidazo[1,2-c]pyrimidine and 2,7-dihydroxy-5-methylthioimidazo[1,2-c]pyrimidine.

Kluge, *J. Heterocyclic Chem.*, 15, 119 (1978), prepared 8-bromomethyl-5-methylimidazo[1,2-c]pyrimidine hydrobromide, 8-hydroxymethyl-5-methylimidazo[1,2-c]pyrimidine, 1-[(5-methylimidazo[1,2-c]pyrimidine-8-yl)-methyl]-2-methylpyridinium bromide hydrobromide, 8-phenylimidazo[1,2-c]pyrimidine and 8-(4-chlorophenyl)-imidazo[1,2-c]pyrimidine. Those compounds were prepared as coccidiostats.

Coburn et al, *J. Heterocyclic Chem.*, 19, 567 (1982), prepared certain imidazo[1,2-c]pyrimidine-2,7-diones.

Turner, U.S. Pat. No. 4,153,695, prepared certain 2,3-dihydroimidazo[1,2-c]pyrimidines substituted by hydrogen, methyl or phenyl substituents in the 2-, 3- and 8-positions; $C_1$–$C_5$ alkyl, phenylamino or methylmercapto in the 5-position; and chloro, pyrrolidino, methylamino or N-methylbenzylamino in the 7-position. These compounds are said to be antiviral agents.

Yanai et al, *Yakagaku Zasshi*, 94(12), 1503–1514 (1974), prepared imidazo[1,2-c]pyrimidine substituted by chloro in the 7-position, or by oxo in the 5-position and hydrogen or methyl in the 7-position.

Schmidt et al, *J. Heterocyclic Chem.*, 7, 715 (1970), prepared 2,7-dichloroimidazo[1,2-c]pyrimidine substituted by chloro, methoxy, methylthio, amino, methylamino or dimethylamino in the 5-position.

Bartholomew et al, *J. Org. Chem.*, 40, 3708 (1975), prepared 2,7-dichloroimidazo[1,2-c]pyrimidin-5-one nucleosides.

In West German Offenlegungsschrift No. 2511316 (laid-open on Sept. 18, 1975), the company Eisai KK has disclosed various 7-hydroxyimidazo[1,2-c]pyrimidines substituted by lower alkyl, unsubstituted phenyl, nitro-substituted phenyl, methylsulphonyl or methoxycarbonyl in the 2-position; and -SR, wherein R is lower alkyl, lower alkenyl or aralkyl in the 5-position. These compounds are said to be anti-inflammatory agents.

Baker et al., *J. Org. Chem.*, 19, 1793–1800 (1954), discloses the compound 4-amino-2-methylthio-6-(1-piperidino)pyrimidine as an intermediate in purine synthesis.

DETAILED DESCRIPTION OF THE INVENTION

The present invention relates to novel imidazo[1,2-c]pyrimidines which are useful bronchodilators. The present invention also relates to pharmacological methods of using these compounds as bronchodilators, pharmaceutical compositions containing these compounds, and novel synthetic intermediates useful in the preparation of these compounds.

The present invention relates to compounds of the Formula I

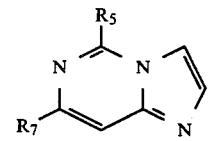

wherein $R_5$ is hydrogen, lower alkyl, lower alkoxy, lower alkylthio, phenyl or

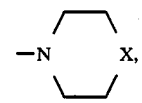

wherein X is oxygen, sulfur, sulfonyl, methylene, imido or N-lower alkylimido; $R_7$ is chloro, lower alkyl, lower alkoxy, N-(lower alkyl)amino, N,N-di(lower alkyl) amino or

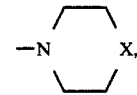

wherein X is oxygen, sulfur, sulfonyl, methylene, imido or N-lower alkylimido; with the proviso that at least one of $R_5$ and $R_7$ is

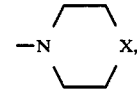

wherein each X is as defined above, or $R_5$ is lower alkoxy and $R_7$ is lower alkoxy or chlorine, or $R_5$ is lower alkylthio and $R_7$ is lower alkyl or N-(lower alkyl)amino or N,N-di(lower alkyl)amino, or $R_7$ is lower alkoxy and $R_5$ is lower alkyl; and pharmaceutically acceptable salts thereof.

The present invention also provides novel compounds of the Formula II

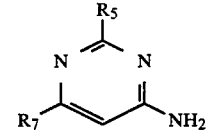

wherein $R_5$ is hydrogen, lower alkyl, phenyl, or

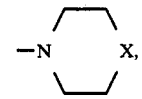

wherein X is oxygen, sulfur, sulfonyl, methylene, imido or N-alkylimido; and $R_7$ is halogen or

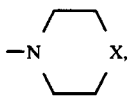

wherein X is oxygen, sulfur, sulfonyl, methylene, imido or N-alkylimido; with the proviso that one and only one of $R_5$ and $R_7$ is

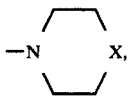

wherein X is as defined above. The compounds of Formula II are useful intermediates in the preparation of certain of the compounds of Formula I.

The present invention further provides novel compounds of the Formula III

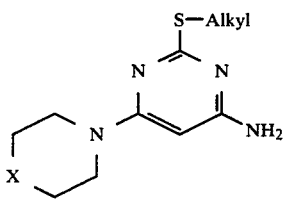

wherein X is oxygen, sulfur, sulfonyl, imido or N-alkylimido; and alkyl is lower alkyl. The compounds of Formula III are also useful intermediates in the preparation of certain of the compounds of Formula I.

The phrase "lower alkyl" as used in the instant specification and claims designates straight and branched-chain alkyl groups containing one to four carbon atoms. Preferred lower alkyl substituents are methyl, ethyl and propyl.

The term "halogen" as used in the instant specification and claims designates fluoro, chloro and bromo.

One presently preferred sub-class of compounds of Formula I are those wherein one or both of $R_5$ and $R_7$ are

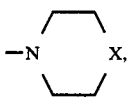

wherein X is as defined above. These compounds are preferred because of generally higher potency in protection against histamine-induced contraction of isolated guinea pig tracheal tissue. This assay is discussed in greater detail below.

Specific preferred compounds are active at a concentration of 10 ug per ml or lower in the abovementioned assay. They are: 7-methyl-5-(4-thiomorpholine)imidazo[1,2-c]pyrimidine; 5-methylthio-7-(4-thiomorpholino)imidazo[1,2-c]pyrimidine; 5-(n-propyl)-7-methoxyimidazo[1,2-c]pyrimidine; 5-methylthio-7-(1-piperidino)imidazo[1,2-c]pyrimidine; 7-methyl-5-methylthioimidazo[1,2-c]pyrimidine; 7-[1-(4-methylpiperazino)]-5-methylthioimidazo[1,2-c]pyrimidine; 5-(n-propyl)-7-(4-thiomorpholino)imidazo[1,2-c]pyrimidine; 7-methyl-5-(4-morpholino)imidazo[1,2-c]pyrimidine; 5-methylthio-7-(4-morpholino)imidazo[1,2-c]pyrimidine; and 5,7-dimethoxyimidazo[1,2-c]pyrimidine.

The bronchodilator activity of compounds of Formula I was assessed by the measurement of effects on isolated tracheal spirals. This is a well-known in vitro test for determining bronchodilator activity. The test was conducted as follows: Female guinea pigs were sacrificed, and each trachea removed and cut into a spiral strip. This strip was mounted in a constant temperature (37° C.) muscle bath of approximately 15 mol volume. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylchloline or barium chloride. The amount of a given compound of Formula I (measured in ug/ml) required to provide greater than 75% relaxation of the drug-induced contraction is considered an effective concentration. For comparison, a well-known standard bronchodilator, aminophylline, requires concentrations of 50 ug/ml versus histamine, 100 ug/ml versus actylcholine and 10 ug/ml versus barium chloride induced contraction.

The compounds of Formula I which were found to be most active in the in vitro test, including some of those listed above as preferred compounds, were tested in vivo in the guinea pig for oral activity using the so-called histamine aerosol method described in U.S. Pat. No. 3,248.292. This test was modified slightly in that a 0.1% aqueous solution of histamine was used as the agent for inducing bronchial constriction. Oral doses were measured in mg/kg of body weight of the guinea pig.

Some of the compounds of Formula I were also found to have activity as mucolytics in an in vitro test for mucus production in which rats are orally dosed with compound prior to sacrifice. The trachea is then isolated and incubated with radio-labelled glucosamine, and the effect of compounds on the incorporation of glucosamine into extracellular mucus is determined. An active compound reduces incorporation of glucosamine.

Some of the compounds of Formula I have also been found to be active as anti-protozoals, including the compounds of Examples 10 and 11.

The compounds of Formula I may be administered to mammals in order to obtain bronchodilation. The compounds may be administered orally or parenterally. Oral administration is preferred except in those instances in which the particular compound is inactive when administered by that route. The usual effective human dose will generally be in the range of about 0.1 to 50 mg/kg of body weight.

Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid in a polar solvent. Isolation of the salt is facilitated by the addition of a solvent in which the salt is insoluble, an example of such a solvent being diethyl ether.

The compounds of Formula I, either as a free base or in the form of a pharmaceutically acceptable acid-addition salt, can be combined with conventional pharmaceutical diluents and carriers to form such dosage forms as tablets, capsules, suspensions, solutions, suppositories and the like. The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Examples of liquid carriers are syrup, peanut oil, olive oil, water and the like. Similarly, the carrier or diluent can include any time delay material well known to the art, such as glyceryl monostearate or glyceryl distearate, these being useful along or, for example, in combination with a wax.

Compounds of Formula I wherein $R_5$ is hydrogen, lower alkyl, lower alkoxy, lower alkylthio,

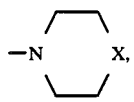

or phenyl and $R_7$ is chloro, lower alkyl,

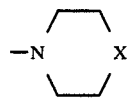

or lower alkoxy may be prepared by Reaction Scheme I illustrated below:

Reaction Scheme I

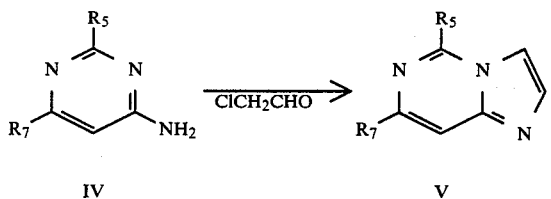

In Reaction Scheme I, a 4-aminopyrimidine of Formula IV is reacted with chloroacetaldehyde to provide a compound of Formula V. Compounds of Formula IV are known or may be readily prepared. For example, the novel compounds of Formula II may be prepared by heating known chloropyrimidines with heterocyclic amines. The reaction is generally carried out by combining the reactants in water or ethanol, followed by heating of the mixture at a temperature of about 80° C. for about one to two hours. The compound of Formula V thereby obtained is isolated by extraction of the reaction mixture with chloroform.

Compounds of Formula I wherein $R_5$ is

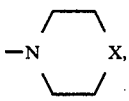

wherein X is oxygen, sulfur, sulfonyl, methylene, imido or N-lower alkylimido, may also be prepared by reacting the corresponding compound wherein $R_5$ is lower alkylthio and $R_7$ is

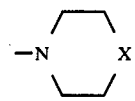

with an amine of the formula

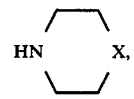

wherein X is as defined above. The reaction is generally carried out by heating at reflux with excess heterocyclic amine.

Using the methods described above the preparation of compounds of the invention is illustrated in the following examples. The purpose of the examples is to enable those skilled in the art to practice the invention, and they are no intended to limit in any way the scope of the invention.

EXAMPLE 1

A mixture of 1.5 g (0.01 mole) of 4-amino-2,6-dimethoxypyrimidine and 3.0 g (0.015 mole) of 50% aqueous chloroacetaldehyde in 20 ml of water was heated at 80° C. for one hour, and was then cooled with an ice bath with concomitant neutralization with sodium bicarbonate. The solid which formed was separated by filtration and recrystallized from cyclohexane with treatment with decolorizing charcoal. White crystals of 5,7-dimethoxyimidazo[1,2-c]pyrimidine, m.p. 120°–121° C., were obtained. Analysis: Calculated for $C_8H_9N_3O_2$: %C, 53.6; %H, 5.1; %N, 23.5; Found: %C, 53.5; %H, 5.0; %N, 23.6. The structural assignment was confirmed by infrared and nuclear magnetic resonance spectral analyses.

EXAMPLE 2

A mixture of 1.7 g (0.011 mole) of 4-amino-6-chloro-2-methoxypyrimidine and 3.0 g (0.015 mole) of 50% aqueous chloroacetaldehyde in 20 ml of water was heated at 80° C. for one hour, and was then cooled in an ice bath with concomitant neutralization with sodium bicarbonate. The mixture was extracted with three 50 ml portions of chloroform which were then dried over magnesium sulfate and evaporated. The residue obtained was dissolved in boiling benzene, treated with decolorizing charcoal, and filtered. The residue which was obtained by evaporation of the filtrate was triturated with diethyl ether to provide a yellow solid. The solid was purified on a preparative scale high pressure liquid chromatograph, using a mixture of 75% ethyl acetate/25% hexanes as the eluent. Recrystallization from cyclohexane gave white solid 7-chloro-5-methoxyimidazo[1,2-c]pyrimidine, m.p. 115°–118° C. Analysis: Calculated for $C_7H_6N_3OCl$: %C,45.8; %H, 3.3; %N, 22.9; Found: %C, 45.4; %H, 3.1; %N, 23.4.

EXAMPLE 3

A mixture of 5 g (32 mmole) of 4-amino-6-methyl-2-methylthiopyrimidine and 10 g (64 mmole) of a 50% aqueous solution of chloroacetaldehyde was heated at 80° C. for one hour. The mixture was cooled with an ice bath and immediately neutralized with sodium bicarbonate. The mixture was extracted with chloroform and the extracts were dried over magnesium sulfate and evaporated to provide an oil. The oil was extracted with hot ethyl acetate, and the extracts were filtered and then evaporated. The residue was dissolved in hot benzene, treated with decolorizing charcoal, and filtered, and the filtrate was evaporated. The residue thereby obtained was dissolved in hot diethyl ether, treated with decolorizing charcoal, and filtered, the filtrate then being evaporated. The residue obtained was recrystallized first from a benzene/hexane mixture and then from cyclohexane, each time accompanied by treatment with decolorizing charcoal. The solid was purified on a preparative scale high pressure liquid chromatograph using ethyl acetate as the eluent. The solid obtained was recrystallized from hexanes to give white crystals of 7-methyl-5-methylthioimidazo[1,2-c]pyrimidine, m.p. 67°–69° C. Analysis: Calculated for $C_8H_9N_3S$: %C, 53.6; %H, 5.1; %N, 23.4; Found: %C, 53.2; %H, 5.0; %N, 23.8.

EXAMPLE 4

A mixture of 3.5 g (0.02 mole) of 4-amino-6-(N-methylamino)-2-methylthiopyrimidine and 4.0 g (0.025 mole) of 50% aqueous chloroacetaldehyde in 50 ml of ethanol was heated at 80° C. for 0.5 hour. The mixture was evaporated, and the residue was extracted with hot ethyl acetate. The residue was then dissolved in 25 ml of water with concomitant treatment with decolorizing charcoal, and the resulting mixture was then filtered. Acetone was added to the filtrate causing precipitation of 7-(N-methylamino)-5-methylthioimidazo[1,2-c]pyrimidine hydrochloride, m.p. 246°–248° C. Analysis: Calculated for $C_8H_{10}N_4S$·HCL: %C, 41.6; %H, 4.8; %N, 21.3; Found: %C, 41.3; %H, 4.8; %N, 21.3.

EXAMPLE 5

A mixture of 2.7 g (0.016 mole) of 4-amino-6-methoxy-2-(n-propyl)pyrimidine and 4.0 g (0.025 mole) of 50% aqueous chloroacetaldehyde in 20 ml of water was heated for one hour at 80° C., and was then cooled in an ice bath with concomitant neutralization with sodium bicarbonate. The mixture was extracted with chloroform, and the extracts were dried over magnesium sulfate and evaporated to provide a residue. The residue was recrystallized from cyclohexane with treatment with decolorizing charcoal. The product was white solid 7-methoxy-5-(n-propyl)imidazo[1,2-c]pyrimidine, m.p. 84°–85° C. Analysis: Calculated for $C_{10}H_{13}N_3O$: %C, 62.8; %H. 6.9; %N, 22.0; Found: %C, 62.6; %H, 6.9; %N, 22.3.

EXAMPLE 6

Using the method of Example 1, 4-amino-6-(4-morpholino)-2-(n-propyl)pyrimidine (prepared as described below in Example 28) was converted to 7-(4-morpholino)-5-(n-propyl)imidazo[1,2-c]pyrimidine. Yellow crystals (m.p. 113°–115° C.) were obtained after two recrystallizations from cyclohexane with concomitant treatment with decolorizing charcoal. Analysis: Calculated for $C_{13}H_{18}N_4O$: C, 63.4; %H, 7.4; %N, 22.8; Found: %C, 62.8; %H, 7.5; %N, 22.8.

EXAMPLE 7

Using the method of Example 1, 4-amino-6-(4-morpholino)-2-phenylpyrimidine (prepared as described below in Example 24) was converted to 7-(4-morpholino)-5-phenylimidazo[1,2-c]pyrimidine. Yellow needles (m.p. 216°–218° C.) were obtained after recrystallization from methanol with treatment with decolorizing charcoal. Analysis: Calculated for $C_{16}H_{16}N_4O$: %C, 68.5; %H, 5.8; %N, 20.0; Found: %C, 68.1; %H, 5.6; %N, 19.9.

EXAMPLE 8

A mixture of 4.5 g (0.016 mole) of 4-amino-2-phenyl-6-(4-thiomorpholino)pyrimidine (prepared as described below in Example 26) and 4.0 g (0.025 mole) of 50% aqueous chloroacetaldehyde in 40 ml of water was heated at 80° C. for one hour, and was then cooled in an ice bath with concomitant neutralization with sodium bicarbonate. The mixture was extracted with chloroform, and the extracts were then evaporated to provide residue which was triturated with ethyl acetate. The product was separated by filtration and recrystallized from acetone with treatment with decolorizing charcoal to provide yellow solid 5-phenyl-7-(4-thiomorpholino)imidazo[1,2-c]-pyrimidine, m.p. 165°–166° C. Analysis: Calculated for $C_{16}H_{16}N_4S$: %C, 64.8; %H, 5.4; %N, 18.9; Found: %C, 64.7; %H, 5.3; %N, 19.0.

EXAMPLE 9

A mixture of 4.8 g (0.2 mole) of 4-amino-2-(n-propyl)-6-(4-triomorphiolino)pyrimidine (prepared as described below in Example 27) and 4.0 g (0.025 mole) of 50% aqueous chloroacetaldehyde in 40 ml of water was heated at 80° C. for 1.5 hours, and was then cooled in an ice bath with concomitant neutralization with sodium bicarbonate. The mixture was extracted with chloroform, and the extracts were then evaporated to provide a residue which was triturated with ethyl acetate. The product was separated by filtration and recrystallized from cyclohexane with treatment with decolorizing charcoal to provide yellow crystals of 5-(n-propyl)-7-(4-thiomorpholino)-imidazo[1,2-c]pyrimidine, m.p. 111°–112.5° C. Analysis: Calculated for $C_{13}H_{18}N_4S$: %C, 59.5; %H, 6.9; %N, 21.4; Found: %C, 59.6; %H, 7.0; %N, 21.4.

EXAMPLE 10

Using the method of Examples 8 and 9, 4-amino-2,6-bis(4-morpholino)pyrimidine was converted to 5,7-bis(4-morpholino)imidazo[1,2-c]pyrimidine. Three recrystallizations from an acetone/hexanes mixture provided a tan solid, m.p. 198°–201° C. Analysis: Calculated for $C_{14}H_{19}N_5O_2$: %C, 58.1; %H, 6,6; %N, 24.2; Found: %C, 57.9; %H, 6.6; %N, 24.0.

EXAMPLE 11

A mixture of 4.3 g (0.017 mole) of 4-amino-2-phenyl-6-(1-piperidono)pyrimidine (prepared as described below in Example 25) and 4.0 g (0.025 mole) of 50% aqueous chloroacetaldehyde in 75 ml of water was heated at 80° C. for one hour, and was then cooled in an ice bath with concomitant neutralization with sodium bicarbonate. The mixture was extracted with chloroform, and the extracts were dried over magnesium sulfate and evaporated to provide a residue which was treated with ethyl acetate and then filtered. The filtrate was evaporated to provide a residue which was taken up in boiling cyclohexane, treated with decolorizing charcoal and filtered while hot. Evaporation provided yellow crystals of 5-phenyl-7-(1-piperidino)-imidazo[1,2-c]pyrimidine, m.p. 142°–144° C. Analysis: Calculated for $C_{17}H_{18}N_4$: %C, 73.4; %H, 6.5; %N, 20.1; Found: %C, 73.5; %H, 6.4; %N, 19.9.

EXAMPLE 12

A mixture of 2.0 g (0.01 mole) of 4-amino-6-(4-thiomorpholino)pyrimidine (prepared as described below in Example 23) and 3.0 g (0.019 mole) of 50% aqueous chloroacetaldehyde in 20 ml of water was heated at 80° C. for 0.5 hour, and was then cooled in an ice bath with concomitant neutralization with sodium bicarbonate. The mixture was extracted with chloroform, and the extracts were dried over magnesium sulfate and evaporated. The residue obtained was triturated with diethyl ether and an off-white solid was thereby obtained. The solid was first crystallized three times from a mixture of benzene and hexanes with treatment with decolorizing charcoal, and was then recrystallized twice for ethyl acetate/hexanes to provide 7-(4-thiomorpholino)imidazo[1,2-c]pyrimidine hydrate, m.p. 158°–160° C. (dec.). Analysis: Calculated for $C_{10}H_{12}N_4S.\frac{1}{2}H_2O$: %C, 52.4; %H, 5.7; %N, 24.4; Found: %C, 52.8; %H, 5.4; %N, 24.1.

EXAMPLE 13

A mixture of 3.2 g (0.018 mole) of 4-amino-6-(4-morpholino)pyrimidine (prepared as described below in Example 22) and 4.0 g (0.025 mole) of 50% aqueous chloroacetaldehyde in 40 ml of water was heated at 80° C. for 0.5 hour, and was then cooled in an ice bath with concomitant neutralization with sodium bicarbonate. The mixture was extracted with dichloromethane, and the extracts were dried over magnesium sulfate and evaporated. The residue obtained was recrystallized from a mixture of ethyl acetate and hexanes with treatment with decolorizing charcoal to provide an off-white solid 7-(4-morpholino)-imidazo[1,2-c]pyrimidine hydrate, m.p. 165°–168° C. (dec.). Analysis: Calculated for $C_{10}H_{12}N_4O.\frac{1}{4}H_2O$: %C, 57.5; %H,6.0; %N,26.8; Found: %C,57.8; %H,5.8; %N,26.7.

EXAMPLE 14

A mixture of 4.0 g (0.015 mole) of 4-amino-6-chloro-2-(4-thiomorpholino-1,1-dioxo)pyrimidine (prepared as described below in Example 29) and 5.0 g (0.03 mole) of 50% aqueous chloroacetaldehyde in 40 ml of water was heated at 80° C. for two hours. An additional 5.0 g of chloroacetaldehyde was added to the mixture, and the mixture was then heated at 80° C. for about 16 hours. The mixture was cooled in an ice bath and neutralized with sodium bicarbonate. The resulting solid was separated by filtration and was recrystallized from ethanol with treatment with decolorizing charcoal and partial evaporation to provide off-white crystals of 7-chloro-5-(4-thiomorpholino-1,1-dioxo)imidazo[1,2-c]-pyrimidine, m.p. 280° C. Analysis: Calculated for $C_{10}H_{11}ClN_4O_2S$: %C,41.9; %H,3.9; %N,19.5; Found: %C,41.9; %H,3.8; %N,19.7.

EXAMPLE 15

A mixture of 4.8 g (0.021 mole) of 4-amino-6-(1-piperidino)-2-methylthiopyrimidine and 4.0 g (0.025 mole) of 50% aqueous chloroacetaldehyde in 50 ml of ethanol was heated at 80° C. for 0.5 hour. The mixture was evaporated, and the residue was extracted with hot ethyl acetate. The residue was dissolved in water, neutralized with sodium carbonate and the solution was extracted with chloroform. The extracts were evaporated, and the residue thereby obtained was recrystallized twice from cyclohexane with treatment with decolorizing charcoal to provide yellow solid 7-(1-piperidino)-5-methylthioimidazo[1,2-c]-pyrimidine. Analysis: Calculated for $C_{12}H_{16}N_4S$: %C,58.0; %H,6.5; %N,22.6; Found: %C,58.0; %H6.6; %N,22.5.

EXAMPLE 16

A mixture of 6.7 g (0.028 mole) of 4-amino-6-[1-(4-methylpiperazino)]-2-methylthiopyrimidine (prepared as described below in Example 37) and 5.0 g (0.03 mole) of 50% aqueous chloroacetaldehyde in 40 ml of ethanol was heated at 80° C. for 0.5 hour. Cooling provided a solid product which was dissolved in a small amount of water, treated with decolorizing charcoal and filtered. The product was forced out of the filtrate by the addition of acetone to provide 7-[1-(4-methylpiperazino)]-5-methylthioimidazo[1,2-c]pyrimidine hydrochloride hydrate, m.p. 285°–288° C. Analysis: Calculated for $C_{12}H_{17}N_5S.HCl.\frac{1}{3}H_2O$: %C,47.1; %H,6.2; %N,22.9; Found: %C,46.8; %H,6.2; %N,22.8.

EXAMPLE 17

A mixture of 4.8 g (0.02 mole) of 4-amino-2-methylthio-6-(4-thiomorpholino)pyrimidine (prepared as described below in Example 36) and 4.0 g (0.025 mole) of 50% aqueous chloroacetaldehyde in 50 ml of ethanol was heated at reflux for 0.5 hour. The mixture was evaporated, and the resulting residue was extracted with ethyl acetate. This residue was then recrystallized from a small volume of methanol to provide off-white crystals of 5-methylthio-7-(4-thiomorpholino)imidazo[1,2-c]pyrimidine hydrochloride hydrate, m.p. 218°–220° C. Analysis: Calculated for $C_{11}H_{14}N_4N_4S_2.HCl.\frac{1}{3}H_2O$; %C,43.2; %H,5.2; %N,18.3; Found: %C,43.2; %H,5.6; %N,18,6.

A 1.0 g sample of the hydrochloride salt was dissolved in water, and the resulting solution was neutralized with sodium carbonate and extracted with chloroform. The extracts were evaporated to provide a residue which was recrystallized from ethyl acetate to provide the free base, m.p. 149°–150° C. Analysis: Calculated for $C_{11}H_{14}N_4S_2$: %C,50.2; %H,5.4; %N,21.3; Found: %C,50.0; %H,5.3; %N,20.8.

EXAMPLE 18

A mixture of 4.5 g (0.02 mole) of 4-amino-2-methylthio-6-(4-morpholino)pyrimidine (prepared as described in Example 35) and 4 g (0.025 mole) of 50% aqueous chloroacetaldehyde in 50 ml of ethanol was heated at 80° C. for 0.75 hour, and was then cooled with an ice bath. The white solid was separated by filtration and recrystallized from methanol to provide 5-methylthio-7-(4-morpholino)-imidazo[1,2-c]pyrimidine hydrochloride, m.p. 235°–239° C. Analysis: Calculated for $C_{11}H_{14}N_4OS.HCl$: %C,46.0; %H,5.3; %N,19.5; Found: %C,46.0; %C, %H,5.4; %N,19.5.

EXAMPLE 19

A mixture of 4.5 g (0.018 mole) of 4-amino-2-methylthio-6-(4-thiomorpholino)pyrimidine (prepared as described below in Example 36) and 4.0 g (0.025 mole) of 50% aqueous chloroacetaldehyde in 50 ml of ethanol was heated at 80° C. for 0.5 hour, and was then cooled and evaporated to provide a crude residue of 5-methylthio-7-(4-thiomorpholino)imidazo[1,2-c]pyrimidine. To the residue was added 25 ml of morpholine and the mixture was heated at reflux for about 16 hours. The mixture was then evaporated and water was added to the residue. The solid was separted by filtration and recrystallized from ethyl acetate with treatment with decolorizing charcoal to give yellow crystals of 5-(4-morpholino)-7-(4-thiomorpholino)imidazo[1,2-c]pyrimidine, m.p. 177°-178° C. Analysis: Calculated for $C_{14}H_{19}N_5OS$: %C,55.1; %H,6.3; %N,22.9; Found: %C,54.7; %H,6.2; %N,22.8.

EXAMPLE 20

Using the method of Example 19, 4-amino-6-methyl-2-methylthiopyrimidine was reacted with chloroacetaldehyde, and the product thereby obtained was reacted with morpholine to provide a dark oil. The oil was purified using a preparative scale high pressure liquid chromatograph and ethyl acetate as the eluent. The product was recrystallized from cyclohexane with treatment with decolorizig charcoal to provide white crystals of 7-methyl-5-(4-morpholino)imidazo[1,2-c]pyrimidine, m.p. 117°-118° C. Analysis: Calculated for $C_{11}H_{18}N_4O$: %C,60.5; %H,6.5; %N,25.7; Found: %C,60.5; %H,6.5; %N,26.0.

EXAMPLE 21

Using the method of Example 19, 4-amino-6-methyl-2-methylthiopyrimidine was reacted with chloroacetaldehyde, and the product thereby obtained was reacted with thiomorpholine to provide a dark oil. The oil was purified by chromatography using a silica gel column, followed by high pressure liquid chromatography using ethyl acetate as the eluent. The product was recrystallized from cyclohexane/ethyl acetate with treatment with decolorizing charcoal to give 7-methyl-5-(4-thiomorpholino)imidazo[1,2-c]pyrimidine, m.p. 129°-131° C. Analysis: Calculated for $C_{11}H_{14}N_4S$: %C,56.4; %H,6.0; %N,23.9; Found: %C,56.3; %H,6.0; %N,23.8.

EXAMPLE 22

A mixture of 8.0 g (0.062 mole) of 4-amino-6-chloropyrimidine and 10.8 g (0.124 mole) of morpholine in 100 ml of torluene was heated at its reflux temperature for 20 hours, and was then cooled. The solid was separated by filtration, washed with toluene, and slurried in 100 ml of water followed by filtration. Recrystallization from water provided yellow crystals of 4-amino-6-(4-morpholino)pyrimidine, m.p. 198°-201° C. Analysis: Calculated for $C_8H_{12}N_4O$: %C,53.3; %H,6.7; %N,31.1; Found: %C,53.5; %H,6.5; %N,31.3.

EXAMPLE 23-32

Using the method of Example 22, the indicated 4-amino-6-chloropyrimidines were reacted with the indicated amines to provide the indicated novel intermediates of Formula IV (TABLE I).

TABLE I

| Example No. | Pyrimidine Intermediate | Amine Reactant | Intermediate of Formula IV (m.p. in °C.) |
|---|---|---|---|
| 23 | 4-amino-6-chloro-pyrimidine | thiomorpholine | 4-amino-6-(4-thiomorpholino)pyrimidine (205-207) |
| 24 | 4-amino-6-chloro-2-phenylpyrimidine | morpholine | 4-amino-6-(4-morpholino)-2-phenylpyrimidine (124-135) |
| 25 | 4-amino-6-chloro-2-phenylpyrimidine | piperidine | 4-amino-2-phenyl-6-(1-piperidino)pyrimidine (no m.p. taken); structure confirmed by NMR analysis |
| 26 | 4-amino-6-chloro-2-phenylpyrimidine | thiomorpholine | 4-amino-2-phenyl-6-(4-thiomorpholino)pyrimidine (no m.p. taken); structure confirmed by NMR analysis |
| 27 | 4-amino-6-chloro-2-(n-propyl)pyrimidine | thiomorpholine | 4-amino-2-(n-propyl)-6-(4-thiomorpholino)-pyrimidine (no m.p. taken); white solid; structure confirmed by IR |
| 28 | 4-amino-6-chloro-2-(n-propyl)pyrimidine | morpholine | 4-amino-2-(n-propyl)-6-(4-morpholino)pyrimidine (no m.p. taken); white solid; structure confirmed by IR |
| 29 | 4-amino-2,6-dichloropyrimidine | thiomorpholine-1,1-dioxide | 4-amino-6-chloro-2(4-thiomorpholino-1,1-dioxo)pyrimidine (218-223) |
| 30 | 4-amino-6-chloro-pyrimidine | piperidine | 4-amino-6-(1-piperidino(pyrimidine (185-187) |
| 31 | 4-amino-6-chloro-pyrimidine | methylamine | 4-amino-6-(N—methylamino)pyrimidine (210-212) |
| 32 | 4-amino-6-chloro-pyrimidine | 4-methylpiperazine | 4-amino-6-[1-(4-methylpiperazino)]-pyrimidine (214-216) |

EXAMPLE 33

To a mixture of 25 ml of methanol and 1.1 g (0.048 mole) of sodium was added 5.1 g (0.030 mole) of 4-amino-6-chloro-2-(n-propyl)pyrimidine, and the resulting mixture was heated at reflux for four days. The mixture was allowed to cool to about 20° C., at which time water and chloroform were added thereto. The layers were separated, and the aqueous layer was extracted with additional chloroform. The organic layers were combined, dried over magnesium sulfate, and evaporated to provide a residue. The residue was recrystallized from cyclohexane with treatment with decolorizing charcoal to provide white solid 4-amino-6-methoxy-2-(n-propyl)pyrimidine, m.p. 97°–99° C. The structural assignment was supported by nuclear magnetic resonance and infrared spectral analyses.

EXAMPLE 34

Using the method of Example 33, 4-amino-6-chloro-2-phenylpyrimidine was reacted with sodium methoxide to provide solid 4-amino-6-methoxy-2-methoxy-2-phenylpyrimidine. The structural assignment was supported by infrared and nuclear magnetic resonance spectral analyses.

EXAMPLE 35

A mixture of 5.2 g (0.02 mole) of 4-amino-6-chloro-2-methylthiopyrimidine and 5.3 g (0.06 mole) of morpholine in 40 ml of ethanol was heated at reflux for fifteen hours. The mixture was then cooled and evaporated. The residue thereby obtained was diluted with water and extracted with dichloromethane. The extracts were dried over magnesium sulfate to provide a residue which was recrystallized with treatment with decolorizing charcoal from a benzene/hexanes mixture to provide 4-amino-2-methylthio-6-(4-morpholino)pyrimidine, m.p. 125°–128° C. The structural assignment was supported by nuclear magnetic resonance spectral analysis.

EXAMPLE 36

Using the method of Example 35, thiomorpholine was reacted with 4-amino-6-chloro-2-methylthiopyrimidine to provide 4-amino-2-methylthio-6-(4-thiomorpholino)pyrimidine as a yellow solid, m.p. 144°–145° C. The structural assignment was supported by nuclear magnetic resonance spectral analysis.

EXAMPLE 37

Using the method of Example 35, 4-methylpiperazine was reacted with 4-amino-6-chloro-2-methylthiopyrimidine to provide white solid 4-amino-6-[1-(4-methylpiperazino)]-2-methylthiopyrimidine, m.p. 165°–167° C. The structural assignment was supported by infrared and nuclear magnetic resonance spectral analyses.

What is claimed is:
1. A compound of the formula

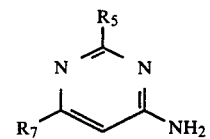

wherein $R_5$ is hydrogen, lower alkyl, phenyl or

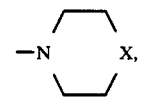

wherein X is sulfur, sulfonyl, imido or N-alkylimido; and $R_7$ is halogen or

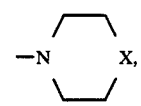

wherein X is sulfur, sulfonyl, imido or N-alkylimido; with the proviso that one and only one of $R_5$ and $R_7$ is

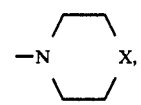

wherein X is as defined above.

2. A compound of the formula

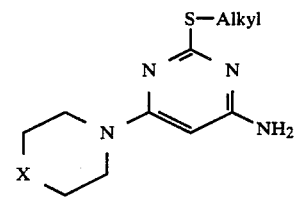

wherein X is oxygen, sulfur, sulfonyl, imido or N-alkylimido; and "Alkyl" is lower alkyl.

* * * * *